United States Patent [19]
Holden et al.

[11] 4,265,890
[45] May 5, 1981

[54] 6-PHENYL THIO- AND 6-CYCLOHEXYL THIO-2,3,4,5-TETRAHYDRO-1H-3-BENZAZEPINES

[75] Inventors: Kenneth G. Holden, Haddonfield; Carl Kaiser, Haddon Heights, both of N.J.

[73] Assignee: Smithkline Corporation, Philadelphia, Pa.

[21] Appl. No.: 39,713

[22] Filed: May 17, 1979

Related U.S. Application Data

[63] Continuation-in-part of Ser. No. 922,613, Jul. 7, 1978, abandoned.

[51] Int. Cl.³ .................. A61K 31/55; C07D 223/16
[52] U.S. Cl. ........................... 424/244; 260/239 BB; 549/59
[58] Field of Search .................. 260/239 BB; 424/244

[56] References Cited

U.S. PATENT DOCUMENTS

| | | | |
|---|---|---|---|
| 3,483,185 | 12/1969 | Tokolicks et al. | 260/239 BB |
| 3,706,830 | 12/1972 | Rodriguez et al. | 424/244 |
| 3,719,669 | 3/1973 | Shetty | 260/239 BB |
| 4,108,989 | 8/1978 | Holden | 424/244 |

*Primary Examiner*—Donald G. Daus
*Assistant Examiner*—D. B. Springer
*Attorney, Agent, or Firm*—Richard D. Foggio; Alan D. Lourie

[57] ABSTRACT

Mercapto substituted-2,3,4,5-tetrahydro-1H-3-benzazepines having dopamine receptor blocking activity are prepared from o-quinones or via standard preparative procedures.

13 Claims, No Drawings

6-PHENYL THIO- AND 6-CYCLOHEXYL THIO-2,3,4,5-TETRAHYDRO-1H-3-BENZAZEPINES

This application is a continuation-in-part of application Ser. No. 922,613 filed July 7, 1978 now abandoned.

This invention relates to novel mercapto substituted-2,3,4,5-tetrahydro-1H-3-benzazepines having pharmacodynamic activity. More specifically the compounds of this invention have dopamine receptor blocking activity and therefore are useful as antipsychotic and antiemetic agents. The antipsychotic activity is similar to that of chlorpromazine.

The compounds of this invention are represented by the following general structural formula:

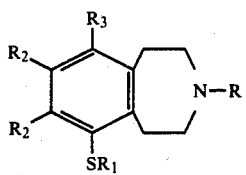

FORMULA I wherein:

R represents methyl, allyl, dimethylallyl, phenethyl, cyclopropylmethyl or β-hydroxyethyl;

$R_1$ represents phenyl, m- or p-substituted phenyl with the substituent being trifluoromethyl, chloro, methoxy, methyl, fluoro, nitro or hydroxy, cyclohexyl, thienyl, thienylmethyl, furyl or furylmethyl;

$R_2$ represents hydrogen, methoxy, alkanoyloxy with the alkanoyl moiety having from 2 to 6 carbon atoms, or hydroxy, each $R_2$ being the same or different except that when one of $R_2$ is alkanoyloxy the other is hydrogen, methoxy or alkanoyloxy; and $R_3$ represents hydrogen, chloro, bromo, trifluoromethyl, fluoro or methyl.

Particular compounds of this invention represented by formula I above are when R is methyl, $R_1$ is phenyl, p-trifluoromethylphenyl, p-chlorophenyl, p-tolyl, p-fluorophenyl, cyclohexyl or 2-thienyl, both $R_2$ are hydrogen, acetoxy or hydroxy, or one $R_2$ is hydroxy and the other is methoxy, and $R_3$ is hydrogen, chloro or bromo.

The pharmaceutically acceptable acid addition salts having the utility of the free bases of Formula I, prepared by methods well known to the art, are formed with both inorganic or organic acids, for example: maleic, fumaric, benzoic, ascorbic, pamoic, succinic, bismethylenesalicyclic, methanesulfonic, ethanedisulfonic, acetic, oxalic, propionic, tartaric, salicyclic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

U.S. Pat. Nos. 3,671,519 and 3,483,185 name "2,3,4,5-tetrahydro-8-methylmercapto-1H-3-benzazepine" as a starting material, however neither of these or equivalent prior art discloses the mercapto substituents of formula I above in a 3-benzazepine series.

The compounds of formula I wherein both $R_2$ are hydroxy are conveniently prepared from dihydroxy substituted benzazepines as shown in the following scheme:

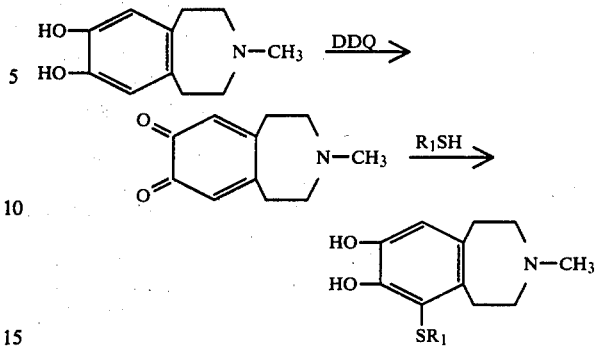

in which $R_1$ is as described above (except for hydroxy substituted phenyl). Thus, a 7,8-dihydroxy substituted benzazepine is oxidized, preferably with 2,3-dichloro-5,6-dicyano-1,4-benzoquinone (DDQ) in an inert organic solvent in which the reactants are soluble such as methanol or ethanol, with chilling at about 0°-5° C. or at ambient temperature until the oxidation is complete. A number of other mild oxidizing agents known to convert catechols to o-quinones may be employed such as, for example, silver oxide, ceric ammonium nitrate, chloranil or silver carbonate. The 7,8-dione intermediate is then reacted with the desired mercaptan ($R_1$SH) in a suitable inert organic solvent such as an alcoholic solvent, methanol or ethanol, at about ambient temperature to give the mercapto substituted product. The hydroxy substituted phenyl products are conveniently obtained from the corresponding methoxy substituted phenyl compounds by treatment with, for example, boron tribromide.

Alternatively the above dihydroxy substituted benzazepine starting material, or its dimethyl ether derivative, is brominated to give the 6-bromo compound which is reacted with n-butyl lithium and then an appropriate disulfide to give the 6-thio substituted product. The ether groups can be cleaved to hydroxy groups by treatment with 48% hydrobromic acid.

The quinone intermediate shown in the above reaction scheme clearly is a valuable intermediate and as such forms a part of this invention.

The methoxy or alkanoyloxy derivatives of formula I ($R_2$) are prepared by alkylation-acylation methods which are conventional to the art. For example, reaction of the 7,8-dihydroxy product obtained as above with diazomethane gives the dimethoxy derivative and with acetyl bromide in triethylamine gives the diacetoxy derivative. Selective demethylation of a 7,8-dimethoxy derivative with, for example, methionine in methanesulfonic acid gives the mixed hydroxy/methoxy products.

To prepare the 7,8-dihydroxy compounds of formula I wherein $R_3$ is chlorine or bromine, the catechol product prepared above is oxidized with DDQ followed by reaction with hydrogen chloride of hydrogen bromide in methanolic solution. Alternatively a chloro or bromo substituted 3-benzazepine may be employed as a suitable starting material. Thus, for example, 3-methyl-7,8-dimethoxy-3-benzazepine is brominated to give the 6,9-dibromo derivative which is reacted with n-butyl lithium followed by the appropriately substituted disulfide to give the 6-thio substituted-9-bromo product. The dimethoxy groups can be cleaved with for example methionine in methanesulfonic acid.

Further, a convenient method of preparation for a 6-chloro catechol product employs an N-protected-7,8-dimethoxy-3-benzazepine as a starting material. For example, N-carboethoxy-7,8-dimethoxy-3-benzazepine is reacted with a sulfenyl chloride under Friedel-Crafts reaction conditions to introduce the 6-phenylthio group and the carboethoxy group is then reduced to methyl with an alkali metal hydride, for example lithium aluminum hydride. The 6-phenylthio group is oxidized with for example periodate to a phenylsulfinyl group and this compound is treated with thionyl chloride to simultaneously introduce the 9-chloro group and reduce the phenylsulfinyl to phenylthio. If desired, the dimethoxy groups can be cleaved with, for example, methionine in methanesulfonic acid.

The 7,8-dihydroxy compounds of formula I wherein $R_3$ is trifluoromethyl are prepared by reacting the corresponding 9-bromo substituted catechol with acetic anhydride to give the 7,8-diacetoxy derivative and treating this with trifluoromethyl iodide in the presence of copper powder in dimethylformamide to give the trifluoromethyl substituted compound, optionally followed by acid hydrolysis with dilute aqueous hydrochloric acid to obtain the unprotected derivatives. Similarly, a 9-bromo-7,8-dimethoxy compound of formula I can be converted to the corresponding 9-methyl product via conversion to the 9-carboxaldehyde, reduction to hydroxymethyl and hydrochloric acid treatment to give the chloromethyl derivative which is then reduced to methyl.

The compounds of formula I wherein $R_2$ and $R_3$ are all hydrogen are conveniently prepared from a halo, such as bromo or chloro, substituted benzazepine by reaction with for example n-butyl lithium followed by the appropriately substituted disulfide. Introduction of an $R_3$ substituent other than hydrogen is accomplished for example by nitration of a chloro substituted benzazepine, displacement of the chlorine by the appropriately substituted mercaptan, followed by reduction of the nitro group, subsequent diazotiazation of the amine and conversion of the diazonium salt to the appropriate $R_3$ substituted derivative. Similarly compounds of formula I wherein one $R_2$ is hydroxy and $R_3$ is hydrogen are obtained from the above described amino substituted benzazepine by diazotization followed by treatment with aqueous sulfuric acid. It will be obvious to one skilled in the art that other combinations of these basic reactions will give compounds of formula I wherein one $R_2$ is hydroxy and $R_3$ is other than hydrogen, as illustrated in the examples below.

The substituent R of the compounds of formula I can be conveniently introduced by reaction with a corresponding N-unsubstituted derivative, for example as shown by the following formula:

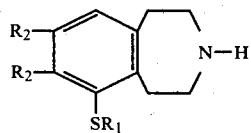

wherein $R_1$ is phenyl and $R_2$ is hydroxy or methoxy. Thus the N-substituted derivative is alkylated or acylated as appropriate to obtain the R substituted products of formula I. The N-unsubstituted derivatives are clearly valuable intermediates, forming a part of this invention, and can be prepared by methods described above for example via the dione or by bromination followed by introduction of the 6-thio substituent through a lithium intermediate.

The dopamine receptor blocking activity of the compounds of this invention is demonstrated by antagonism of avoidance acquisition in rats and/or block of the effects of dopamine on dopamine sensitive adenylate cyclase in rat striatal homogenate. Central dopamine receptor blocking activity is a measure of potential antipsychotic activity. In the pharmacological procedure used to measure antagonism of avoidance acquisition, naive male rats are given either a test compund or saline at a suitable time period prior to testing. The rats are then placed in a dark soundproof box with a grid flood through which footshock is delivered. Trials begin at 30-second intervals. The beginning of each trial is signaled by a light and a buzzer which continues for 10 seconds, at which time footshock is added for an additional 15 seconds. In each trial a single lever press by the animal terminates the sequence. Evaluation of drug activity is based on the number of trials in which the animals fail to avoid or fail to escape footshock during the last 40 trials of a 100 trial, 50-minute session. The $ED_{50}$ is defined as that dose of drug calculated to reduce the number of avoidance responses during the last 40 trials to 50% of the (pooled) control value.

As an example of the antipsychotic activity of the compounds of formula I, the $ED_{50}$ values in mg/kg, i.p. obtained from testing the indicated compounds in the above procedure are as follows:

7,8-dihydroxy-3-methyl-6-phenylthio-2,3,4,5-tetrahydro-1H-3-benzazepine, $ED_{50}$ 0.5;

6-cyclohexylthio-7,8-dihydroxy-3-methyl-2,3,4,5-tetrahydro-1H-3-benzazepine, $ED_{50}$ 1.0;

9-chloro-7,8-dihydroxy-3-methyl-6-phenylthio-2,3,4,5-tetrahydro-1H-3-benzazepine, $ED_{50}$ 0.08;

7,8-dihydroxy-3-methyl-6-(p-trifluoromethylphenylthio)-2,3,4,5-tetrahydro-1H-3-benzazepine, $ED_{50}$ 1.6;

3-methyl-6-phenylthio-2,3,4,5-tetrahydro-1H-3-benzazepine, $ED_{50}$ 1.6;

7,8-dihydroxy-3-methyl-6-(2-thienylthio)-2,3,4,5-tetrahydro-1H-3-benzazepine, $ED_{50}$ 0.14;

8-hydroxy-7-methoxy-3-methyl-6-phenylthio-2,3,4,5-tetrahydro-1H-3-benzazepine, $ED_{50}$ 0.26;

7,8-dihydroxy-6-(p-fluorophenylthio)-3-methyl-2,3,4,5-tetrahydro-1H-3-benzazepine, $ED_{50}$ 0.18;

7,8-dihydroxy-3-methyl-6-(p-tolylthio)-2,3,4,5-tetrahydro-1H-3-benzazepine, $ED_{50}$ 1.2;

9-bromo-7,8-dihydroxy-3-methyl-6-phenylthio-2,3,4,5-tetrahydro-1H-3-benzazepine, $ED_{50}$ 0.18 and 7,8-dihydroxy-6-furfurylthio-3-methyl-2,3,4,5-1H-3-benzazepine, $ED_{50}$ 1.2.

For comparison, chlorpromazine has an Avoidance $ED_{50}$ of 1.5 mg/kg, i.p.

The compounds of formula I wherein both $R_2$ are hydroxy (catechols) have antiemetic activity as demonstrated by anti-apomorphine activity in dogs. In this pharmacological procedure, a test compound is administered subcutaneously to one or more groups of test animals (pre-selected for their sensitivity to apomorphine) while another group serves as controls. After a suitable pretreatment time, apomorphine hydrochloride is administered to each animal in a dosage of 0.1 mg/kg, s.c. Frequency of emesis is observed and recorded over the next 40 minutes. The mean frequency of emesis is calculated for each test group and compared with the controls. Final results are reported as a percentage change in emetic frequency of the test animals relative to the controls. A test compound is considered active if it produces at least a 20% change in emetic frequency of the test animals from that of the controls. The catechols have antiemetic $ED_{50}$ values (that is, reduce emetic frequency by 50% over controls) of less than 1 mg/kg, s.c.

The compounds of this invention may be administered as pharmaceutical compositions in conventional dosage unit forms. These compositions which form a part of this invention are prepared by incorporating a compound of formula I, or a pharmaceutically acceptable acid addition salt thereof, in a nontoxic amount sufficient to produce dopamine receptor blocking activity in an animal or human subject, with a nontoxic pharmaceutical carrier according to accepted procedures. Preferably the compositions will contain the active ingredient in an active but nontoxic amount selected from about 1 mg. to about 300 mg. of active ingredient per dosage unit.

The pharmaceutical carrier employed may be, for example, either a solid or liquid, giving rise to a wide variety of pharmaceutical forms. If a solid pharmaceutical carrier is used, such as lactose, magnesium stearate, terra alba, sucrose, talc, stearic acid, gelatin, agar, pectin, acacia and the like, the composition can be tableted, used as a pharmaceutical powder, placed in a hard gelatin capsule or in the form of a troche or lozenge. The amount of solid carrier will vary widely but preferably will be from about 25 mg. to about 1 g. If a liquid pharmaceutical carrier is used, such as syrup, peanut oil, olive oil, sesame oil, water and the like, the composition will be in the form of a soft gelatin capsule, syrup, emulsion or a liquid suspension. Similarly the carrier or diluent may include a time delay material such as glyceryl monostearate or glyceryl distearate alone or with a wax.

Parenteral dosage forms such as for intramuscular administration are obtained by dissolving a water soluble salt of the active medicament in water or saline solution in a concentration such that 1 ml. of the solution contains from about 2 mg. to about 50 mg. of active ingredient. The solution can then be filled into single ampuls or multiple dose vials.

The pharmaceutical preparations are made following the conventional techniques of the pharmaceutical chemist involving mixing, granulating and compressing when necessary, or variously mixing and dissolving the ingredients as appropriate to give the desired end product.

To produce dopamine receptor blocking activity, a compound of formula I or a pharmaceutically acceptable acid addition salt thereof, usually combined with a pharmaceutical carrier, is administered internally to an animal or human subject in need of such activity in a non-toxic amount sufficient to produce said activity. The route of administration may be oral or parenteral. Advantageously equal doses will be administered until a desired effect is obtained, for example two or three times a day, with the daily dosage regimen being selected from about 2 mg. to about 900 mg. of active ingredient.

The following examples illustrate the preparation of specific compounds and pharmaceutical compositions of this invention and as such are not to be construed as limitations thereof. Those skilled in the art will appreciate that other modifications of the synthetic procedures described and the use of alternative starting materials may also be employed to prepare the compounds of formula I.

EXAMPLE 1

To a cooled solution of aminoacetaldehyde dimethylacetal (21 g., 0.2 mole) and dicyclohexylcarbodiimide (42.5 g., 0.205 mole) in 500 ml. of methylene chloride was added homoveratric acid (39.2 g., 0.2 mole) portionwise with cooling and stirring. After the addition was completed, the reaction mixture was stirred at room temperature for ½ hour, kept in refrigerator overnight and filtered. The filtrate was evaporated to dryness to give an oil which was chilled to form the solid N-(2,2-dimethoxyethyl)-3,4-dimethoxyphenylacetamide, m.p. 60°–63° C.

The acetamide (40 g.) was mixed with 200 ml. of concentrated hydrochloric acid and 200 ml. of glacial acetic acid and allowed to stand at room temperature overnight. The reaction mixture was poured into ice/water and the resulting solid was washed with water/methanol to give 2,3-dihydro-7,8-dimethoxy-2-oxo-1H-3-benzazepine, m.p. 239°–241° C.

The benzazepine (12 g.) was dissolved in 120–130 ml. of glacial acetic acid by heating and then poured into a Parr bottle. To the solution was added 0.8 g. of 10% palladium-on-carbon and the mixture was hydrogenated for 1 to 1½ hours. The catalyst was filtered off and the filtrate was evaporated to dryness to give the 7,8-dimethoxy-2-oxo-2,3,4,5-tetrahydro-1H-3-benzazepine, m.p. 190°–192° C.

To a suspension of the tetrahydrobenzazepine (22 g., 0.1 mole) in 250 ml. of dry tetrahydrofuran was added 225 ml. of 0.94 M diborane, slowly. After addition was completed the mixture was refluxed for 1 hour, cooled, dilute hydrochloric acid added and then heated on a steam bath for 30–40 minutes. The residue was diluted with water, made basic with 10% sodium hydroxide solution and extracted with ethyl acetate. The dried extract was evaporated and the solid was converted to its hydrochloride salt, 7,8-dimethoxy-2,3,4,5-tetrahydro-1H-3-benzazepine hydrochloride, m.p. 240°–241° C.

The tetrahydrobenzazepine (12.3 g) was mixed with 200 ml. of 48% hydrobromic acid and refluxed for 1–2 hours. The reaction mixture was evaporated to dryness and azeotroped with toluene to yield 7,8-dihydroxy-2,3,4,5-tetrahydro-1H-3-benzazepine hydrobromide, m.p. 278°–280° C.

To 300 ml. of a methanolic solution of the dihydroxybenzazepine hydrobromide (9.7 g) was added a slight molar excess of 2,3-dichloro-5,6-dicyano-1,4-benzoquinone, portionwise under nitrogen. The mixture was stirred at room temperature for ½ hour, chilled in an ice bath and filtered to give 2,3,4,5-tetrahydro-1H-3-benzazepine-7,8-dione hydrobromide.

To 500 ml. of a methanolic solution of thiophenol (6.4 g., 0.058 mole) was added the above dione hydrobromide, portionwise. The resulting solution was stirred at room temperature under nitrogen for 1 hour and then evaporated to dryness. The residual oil was stirred with ether and triturated with ethanol to furnish 7,8-dihydroxy-6-phenylthio-2,3,4,5-tetrahydro-1H-3-benzazepine hydrobromide, m.p. 125°–128° C. This catechol can be converted to 3-substituted products of formula I.

EXAMPLE 2

A mixture of 7,8-dimethoxy-2,3,4,5-tetrahydro-1H-3-benzazepine (19.5 g., 0.094 mole), 78 ml. of 37% formaldehyde and 117 ml. of 99–100% formic acid was refluxed overnight and then evaporated to dryness. Dilute hydrochloric acid (140 ml.) was added to the resulting residue and evaporated to dryness again. This residue was treated with 140 ml. of 10% sodium hydroxide solution and extracted with ethyl acetate. The extract was washed, dried and the residue converted to its hydrochloride salt to give 7,8-dimethoxy-3-methyl-2,3,4,5-tetrahydro-1H-3-benzazepine hydrochloride, m.p. 250°–254° C.

The above 3-methylbenzazepine (5.2 g., 0.02 mole) was mixed with 100 ml. of 48% hydrobromic acid and refluxed for 1 to 1½ hours. The reaction mixture was evaporated to dryness and azeotroped with toluene to leave 7,8-hydroxy-3-methyl-2,3,4,5-tetrahydro-1H-3-benzazepine hydrobromide, m.p. 230°–233° C. (decomp.).

To a solution of 16 g. (0.0584 mole) of the dihydroxybenzazepine in 300 ml. of methanol was added, portionwise, 14.3 g. (0.063 mole) of 2,3-dichloro-5,6-dicyano-1,4-benzoquinone under nitrogen and the mixture stirred at room temperature for 1 hour. The reaction mixture was chilled in an ice-bath and filtered to give 3-methyl-2,3,4,5-tetrahydro-1H-3-benzazepine-7,8-dione hydrobromide.

To a methanolic solution (200 ml.) of thiophenol (1.92 g., 0.0175 mole) was added 2.2 g. (0.0081 mole) of the above dione portionwise and the resulting solution was stirred at room temperature under nitrogen for 1 hour. The reaction mixture was evaporated to leave 7,8-dihydroxy-3-methyl-6-phenylthio-2,3,4,5-tetrahydro-1H-3-benzazepine hydrobromide, m.p. 116°–120° C.; free base m.p. 174° C.

Following the above procedure and reacting the dione with cyclohexylmercaptan, m-trifluoromethylthiophenol, p-trifluoromethylthiophenol or p-chlorothiophenol yielded the respective products: 6-cyclohexylthio-7,8-dihydroxy-3-methyl-2,3,4,5-tetrahydro-1H-3-benzazepine, m.p. 148°–157° C.; 7,8-dihydroxy-3-methyl-6-(m-trifluoromethylphenylthio)-2,3,4,5-tetrahydro-1H-3-benzazepine, m.p. 183°–185° C.; 7,8-dihydroxy-3-methyl-6-(p-trifluoromethylphenylthio)-2,3,4,5-tetrahydro-1H-3-benzazepine fumarate m.p. 222° C.; and 6-(p-chlorophenylthio)-7,8-dihydroxy-3-methyl-2,3,4,5-tetrahydro-1H-3-benzazepine, hemifumarate m.p. 209°–211° C.

EXAMPLE 3

To a methanolic suspension of 7,8-dihydroxy-3-methyl-6-phenylthio-2,3,4,5-tetrahydro-1H-3-benzazepine (1.0 g., 0.0033 mole) was added, portionwise, diazomethane generated in the conventional way using N-methyl-N'-nitro-N-nitrosoguanidine. The mixture was stirred at room temperature for 1 hour, excess diazomethane was removed under a stream of nitrogen and then concentrated. Fumaric acid dissolved in a minimum amount of methanol was added and the solution chilled to give 7,8-dimethoxy-3-methyl-6-phenylthio-2,3,4,5-tetrahydro-1H-3-benzazepine fumarate, m.p. 181°–184° C.

EXAMPLE 4

A solution of 3.2 g. of 7,8-dihydroxy-3-methyl-6-phenylthio-2,3,4,5-tetrahydro-1H-3-benzazepine in about 500 ml. of dry benzene was stirred at room temperature for 15 minutes and then 4.5 ml. of triethylamine was added. Acetyl bromide (5.4 g., 0.044 mole) in 20 ml. of benzene was added dropwise and the mixture refluxed for 1½ hours. The reaction mixture was evaporated to dryness and the residue partitioned between 5% sodium bicarbonate solution and ethyl acetate. The ethyl acetate solution was washed, dried and evaporated. The residue was treated with fumaric acid to yield 7,8-diacetoxy-3-methyl-6-phenylthio-2,3,4,5-tetrahydro-1H-3-benzazepine fumarate, m.p. 156°–161° C.

Similarly 6-cyclohexylthio-7,8-dihydroxy-3-methyl-2,3,4,5-tetrahydro-1H-3-benzazepine was reacted with acetyl bromide as described above to give 7,8-diacetoxy-6-cyclohexylthio-3-methyl-2,3,4,5-tetrahydro-1H-3-benzazepine; hydrobromide salt m.p. 149°–150° C.

EXAMPLE 5

To a mixture of 7 g. (0.0337 mole) of 7,8-dimethoxy-2,3,4,5-tetrahydro-1H-3-benzazepine dissolved in 170 ml. of acetonitrile and 5 ml. of triethylamine, cooled in an ice bath, was added 4.25 g. (0.035 mole) of allyl bromide in 30 ml. of acetonitrile, dropwise with stirring. The mixture was brought to room temperature and refluxed for 1½ hours. The reaction mixture was evaporated to dryness, partitioned between ethyl acetate and 5% sodium bicarbonate solution, and the separated ethyl acetate dried and evaporated to give 3-allyl-7,8-dimethoxy-2,3,4,5-tetrahydro-1H-3-benzazepine.

The 3-allyl benzazepine (4.5 g., 0.0182 mole) was dissolved in 200 ml. of methylene chloride, cooled and 9 g. (0.036 mole) of boron tribromide in 45 ml. of methylene chloride was added dropwise. The mixture was stirred in the ice bath for 30 minutes and then at room temperature for 1 hour. Excess boron tribromide was destroyed by adding methanol and the mixture evaporated to dryness. The residue was triturated with acetonitrile to yield 3-allyl-7,8-dihydroxy-2,3,4,5-tetrahydro-1H-3-benzazepine hydrobromide, m.p. 195°–204° C.

Following the procedures outlined in Example 2 the 3-allyl-7,8-dihydroxy-2,3,4,5-tetrahydro-1H-3-benzazepine hydrobromide was treated with 2,3-dichloro-5,6-dicyano-1,4-benzoquinone to give the 7,8-dione which was then reacted with, for example, thiophenol to obtain the corresponding 3-allyl-7,8-dihydroxy-6-phenylthio-2,3,4,5-tetrahydro-1H-3-benzazepine hydrobromide, m.p. 103°–123° C.

Similarly, reaction of dimethylallyl bromide as described above gives as the final product 7,8-dihydroxy-3-dimethylallyl-6-phenylthio-2,3,4,5-tetrahydro-1H-3-benzazepine hydrobromide.

EXAMPLE 6

A solution of 5 g. (0.0166 mole) of 7,8-dihydroxy-3-methyl-6-phenylthio-2,3,4,5-tetrahydro-1H-3-benzazepine in 250 ml. of methanol was acidified with ethereal hydrogen chloride to yield the hydrochloride salt. The latter was dissolved in 300 ml. of methanol and 4.0 g. (0.0176 mole) of 2,3-dichloro-5,6-dicyano-1,4-benzoquinone was added portionwise under nitrogen and the mixture stirred at room temperature for 20 minutes. Ether was added to the reaction mixture and the solvents decanted to leave 3-methyl-6-phenylthio-2,3,4,5-tetrahydro-1H-3-benzazepine-7,8-dione hydrochloride. This hydrochloride was dissolved in a minimum amount of methanol and then added to a methanolic hydrogen chloride solution, portionwise. The mixture was stirred at room temperature for 1 hour, the solvent was evaporated and the residue triturated with acetonitrile. The separated solid was purified via conversion to its free base to give 9-chloro-7,8-dihydroxy-3-methyl-6-phenylthio-2,3,4,5-tetrahydro-1H-3-benzazepine, m.p. 173°–174° C.

EXAMPLE 7

To a stirred solution of 2-thiophenethiol (0.9 g., 0.0076 mole) in 200 ml. of methanol was added portionwise 2 g. (0.0074 mole) of 3-methyl-2,3,4,5-tetrahydro-1H-3-benzazepine-7,8-dione, at room temperature under argon. After stirring for 1 hour, the methanol was distilled under vacuum, the residue slurried in 30 ml. of water and filtered. The filtrate was made basic to give the product, 7,8-dihydroxy-3-methyl-6-(2-thienylthio)-2,3,4,5-tetrahydro-1H-3-benzazepine, m.p. 189°–191° C.

Similarly the above dione (5 g., 0.018 mole) was added portionwise to a solution of 2.3 g. (0.02 mole) of 3-thiophenethiol in 200 ml. of methanol to yield upon workup the corresponding product, 7,8-dihydroxy-3-methyl-6-(3-thienylthio)-2,3,4,5-tetrahydro-1H-3-benzazepine, m.p. 189°–191° C.

EXAMPLE 8

A stirred solution of 620 ml. of 0.9 M n-butyl lithium (0.56 mole) in tetrahydrofuran is placed under nitrogen and cooled to −70° C. To this stirred solution is added dropwise, during a period of 30 minutes, a solution of 0.1 mole of 6-bromo-3-methyl-2,3,4,5-tetrahydro-1H-3-benzazepine in 230 ml. of tetrahydrofuran. The solution is stirred at −70° C. for 30 minutes and then a solution of 135 g. (0.62 mole) of diphenyldisulfide in 385 ml. of tetrahydrofuran is added dropwise. Stirring at −70° C. is continued for 1 hour. The nearly colorless solution is poured slowly with stirring into 5 l. of ice/water containing excess hydrochloric acid. The mixture is extracted with ether, then the aqueous phase is made alkaline by addition of 10 N sodium hydroxide. An ether extract of the resulting mixture is washed with a saturated solution of sodium chloride, dried over magnesium sulfate and concentrated. The residual liquid is subjected to chromatographic separation to afford 3-methyl-6-phenylthio-2,3,4,5-tetrahydro-1H-3-benzazepine, which is converted to a cyclohexylsulfamic acid salt in methanol-ether, m.p. 136°–139° C.

EXAMPLE 9

To a stirred mixture of 400 g. of concentrated sulfuric acid and 100 g. of concentrated nitric acid at 0°–5° C. is added, in portions, 19.6 g. (0.1 mole) of 6-chloro-3-methyl-2,3,4,5-tetrahydro-1H-3-benzazepine. The solution is stirred at 0°–5° C. for 2.5 hours, then it is poured cautiously into 1.5 liters of ice/water. The solution is made basic by addition of excess sodium hydroxide, then it is extracted with ether. After being washed several times with water the extract is dried and concentrated. The resulting mixture of approximately equal parts of 6-chloro-3-methyl-9-nitro-2,3,4,5-tetrahydro-1H-3-benzazepine and 6-chloro-3-methyl-7-nitro-2,3,4,5-tetrahydro-1H-3-benzazepine is separated by chromatographic methods.

To a stirred solution of 11.0 g. (0.1 mole) of thiophenol in 200 ml. of dimethylformamide at 0°–10° C., under an atmosphere of nitrogen, is added cautiously, in portions, 4.65 g. (0.11 mole) of a 57% dispersion of sodium hydride in mineral oil. The resulting solution is stirred for 15 minutes at 25° C. and then a solution of 24.1 g. (0.1 mole) of 6-chloro-3-methyl-9-nitro-2,3,4,5-tetrahydro-1H-3-benzazepine in 50 ml. of dimethylformamide is added dropwise. The reaction mixture is heated at 100° C. for 2 hours, then it is cooled to 25° C. and poured into ice/water. The resulting solid is filtered, air-dried and recrystallized from ethyl acetate-hexane to give 3-methyl-9-nitro-6-phenylthio-2,3,4,5-tetrahydro-1H-3-benzazepine.

To a solution of 15.7 g. (0.05 mole) of 3-methyl-9-nitro-6-phenylthio-2,3,4,5-tetrahydro-1H-3-benzazepine in 350 ml. of ethanol and 125 ml. of water is added, in portions, 35 g. (0.2 mole) of sodium hydrosulfite. The mixture is stirred and refluxed for 16 hours, then an additional 52 g. (0.3 mole) of sodium hydrosulfite is added and refluxing is continued for 30 hours, allowing about one-half of the solvent to distill from the reaction during the last hour. The mixture is cooled, diluted with water, made alkaline with ammonium hydroxide and extracted with ethyl acetate. After being dried, the extract is concentrated to give 9-amino-3-methyl-6-phenylthio-2,3,4,5-tetrahydro-1H-3-benzazepine which is purified by chromatography. A solution of the base in ethanol is treated with an excess of hydrogen chloride. Following addition of ether crystalline 9-amino-3-methyl-6-phenylthio-2,3,4,5-tetrahydro-1H-3-benzazepine dihydrochloride is obtained.

Alternatively the 9-nitro compound is hydrogenated in ethanol solution with 5% palladium-on-carbon at 50 p.s.i. for 2 hours to give the 9-amino derivative.

To a stirred suspension of 17.9 g. (0.05 mole) of 9-amino-3-methyl-6-phenylthio-2,3,4,5-tetrahydro-1H-3-benzazepine dihydrochloride in 50 ml. of water and 50 ml. of concentrated hydrochloric acid at 0°–5° C. is added dropwise a solution of 4.2 g. (0.06 mole) of sodium nitrite in 25 ml. of water. After being stirred at 0°–5° C. for 30 minutes, the resulting diazonium solution is added to a solution of 6.0 g. (0.06 mole) of cuprous chloride in 25 ml. of concentrated hydrochloric acid. The mixture is stirred for 16 hours at 25° C., then it is warmed to 60°–80° C. for 1 hour. After being cooled to 15°–20° C., the mixture is made alkaline and extracted with ether. The ether extract is dried over magnesium sulfate and concentrated to leave 9-chloro-3-methyl-6-phenylthio-2,3,4,5-tetrahydro-1H-3-benzazepine which is purified by chromatography or by recrystallization of appropriate acid addition salts; hydrochloride salt m.p. 231°–232° C.

EXAMPLE 10

To a stirred solution of 114 ml. of water and 15 ml. of concentrated sulfuric acid at 60°–70° C. is added 23.2 g. (0.082 mole) of 9-amino-3-methyl-6-phenylthio-2,3,4,5-tetrahydro-1H-3-benzazepine. The resulting suspension is stirred vigorously and cooled to 0°–5° C. To this suspension is added 6.3 g. (0.091 mole) of sodium nitrite in 10 ml. of water at a rate such that the temperature does not exceed 5° C. The resulting diazonium solution is added dropwise to a boiling solution of 200 g. of cuprous sulfate and 300 ml. of water. After being refluxed for 15 minutes the solution is cooled, a trace of ascorbic acid is added and the pH is adjusted to 7.0 with ammonium hydroxide. The mixture is extracted with ethyl acetate. After being dried the extract is concentrated to afford 9-hydroxy-3-methyl-6-phenylthio-2,3,4,5-tetrahydro-1H-3-benzazepine. Purification is accomplished by chromatography or by recrystallization of an appropriate acid addition salt.

EXAMPLE 11

Following the procedures outlined in Example 9, the isomeric 6-chloro-3-methyl-7-nitro-2,3,4,5-tetrahydro-1H-3-benzazepine is treated with sodium thiophenolate to give the 6-phenylthio intermediate and the nitro group is reduced with sodium hydrosulfite. To a solution of 2.6 g. (0.0125 mole) of the resulting 7-amino-3-methyl-6-phenylthio-2,3,4,5-tetrahydro-1H-3-benzazepine in 25 ml. of 3 N sulfuric acid at 0°–3° C., a solution of sodium nitrite (1 g. in 5 ml. of water) is added dropwise until a positive test for nitrous acid is obtained. Excess nitrous acid is decomposed by adding 0.2 to 0.3 g. of urea and stirring for 10 minutes. The diazonium solution is added dropwise with stirring to 200 ml. of 50% sulfuric acid at 70° C. and maintained at 70° C. until all of the diazonium salt is decomposed. On cooling the warm solution in an ice bath a crystalline precipitate is formed. After being chilled for 30 minutes at 0° C., the mixture is filtered. The solid is washed with a small volume of ice/water. Recrystallization affords 7-hydroxy-3-methyl-6-phenylthio-2,3,4,5-tetrahydro-1H-3-benzazepine sulfate.

EXAMPLE 12

A suspension of 12.0 g. (0.05 mole) of 6-chloro-3-methyl-9-nitro-2,3,4,5-tetrahydro-1H-3-benzazepine, 100 ml. of ethanol and 0.2 g. of platinum dioxide is hydrogenated on a Parr apparatus at 25° C. and an initial hydrogen pressure of 60 p.s.i. After the rapid hydrogen uptake is completed, the mixture is filtered and the filtrate is concentrated in vacuo to give 9-amino-6-chloro-3-methyl-2,3,4,5-tetrahydro-1H-3-benzazepine.

A mixture of 10.5 g. (0.05 mole) of 9-amino-6-chloro-3-methyl-2,3,4,5-tetrahydro-1H-3-benzazepine and 50 ml. of acetic anhydride is stirred and heated at 60°–65° C. for 4 hours. The resulting solution is poured into ice/water and stirred at 25° C. for 16 hours, then it is made alkaline by addition of sodium hydroxide at 5°–10° C. The precipitate is immediately filtered to give 9-acetamido-6-chloro-3-methyl-2,3,4,5-tetrahydro-1H-3-benzazepine.

To a stirred mixture of 200 g. of concentrated sulfuric acid and 50 g. of concentrated nitric acid at 0°–5° C. is added, in portions, 12.6 g. (0.05 mole) of 9-acetamido-6-chloro-3-methyl-2,3,4,5-tetrahydro-1H-3-benzazepine. The solution is stirred at 0°–5° C. for 2 hours and then it is poured cautiously into 500 ml. of ice/water. The solution is made alkaline with sodium hydroxide. After being stirred at 25° C. for 16 hours, the mixture is filtered to give 9-amino-6-chloro-3-methyl-8-nitro-2,3,4,5-tetrahydro-1H-3-benzazepine.

A solution of 100 ml. of sulfuric acid and 50 ml. of water is cooled to −10° C. and maintained at this temperature while 3.7 g. (0.054 mole) of sodium nitrite is added in small portions over a period of about 15 minutes. Cold 50% hypophosphorous acid 19.3 ml., (0.186 mole) is added over a period of 10–15 minutes, the temperature still being maintained at −10° C. A solution of 5.1 g. (0.02 mole) of 9-amino-6-chloro-3-methyl-8-nitro-2,3,4,5-tetrahydro-1H-3-benzazepine in 100 ml. of glacial acetic acid is then added to the stirred diazonium solution dropwise during a period of 1 hour as the temperature is maintained at −10° C. Stirring is continued for 2 hours allowing the temperature to rise to 5° C. The solution is maintained at this temperature in a hood for 36 hours, then the solution is steam distilled to remove acetic acid. The residual liquid is cooled and sodium hydroxide is cautiously added with stirring. The crystalline 6-chloro-3-methyl-8-nitro-2,3,4,5-tetrahydro-1H-3-benzazepine is filtered. It may be purified by chromatography or recrystallization from ethyl acetatehexane.

A stirred solution of 62 ml. of 0.9 M n-butyl lithium (0.056 mole) in tetrahydrofuran, under nitrogen, is cooled to −70° C. and a solution of 2.4 g. (0.01 mole) of 6-chloro-3-methyl-8-nitro-2,3,4,5-tetrahydro-1H-3-benzazepine in 25 ml. of tetrahydrofuran is added during a period of 30 minutes. The solution is stirred at −70° C. for 30 minutes and then a solution of 13.5 g. (0.06 mole) of diphenyldisulfide in 40 ml. of tetrahydrofuran is added dropwise. After being stirred at −70° C. for 1 hour the solution is poured into 500 ml. of ice/water containing excess hydrochloric acid. The mixture is extracted with ethyl acetate and then the aqueous phase is made alkaline with 10 N sodium hydroxide to precipitate 3-methyl-8-nitro-6-phenylthio-2,3,4,5-tetrahydro-1H-3-benzazepine. The product is filtered and recrystallized from ethyl acetate-hexane or aqueous ethanol.

Following the procedures outlined in Examples 9 and 10, the 3-methyl-8-nitro-6-phenylthio-2,3,4,5-tetrahydro-1H-3-benzazepine is reduced with sodium hydrosulfite and the corresponding 8-amino derivative is diazotized and then heated with cuprous sulfate/sulfuric acid to yield 8-hydroxy-3-methyl-6-phenylthio-2,3,4,5-tetrahydro-1H-3-benzazepine.

EXAMPLE 13

Following the procedures outlined in Example 12, 9-amino-6-chloro-3-methyl-8-nitro-2,3,4,5-tetrahydro-1H-3-benzazepine is treated with n-butyl lithium followed by diphenyldisulfide to give the corresponding 6-phenylthio derivative which is diazotized and then reacted with cuprous chloride and hydrochloric acid to give 9-chloro-8-nitro-3-methyl-6-phenylthio-2,3,4,5-tetrahydro-1H-3-benzazepine. The latter is reduced with sodium hydrosulfite and the resulting 8-amino derivative is diazotized and then treating with cuprous sulfate/sulfuric acid to furnish 9-chloro-8-hydroxy-3-methyl-6-phenylthio-2,3,4,5-tetrahydro-1H-3-benzazepine.

EXAMPLE 14

The free base of 7,8-dimethoxy-3-methyl-2,3,4,5-tetrahydro-1H-3-benzazepine (0.075 mole) is dissolved in 170 ml. of acetic acid. Bromine (28 g., 0.175 mole) is added in a thin stream and the mixture is stirred for 2 hours. The precipitate is collected, washed with ether and dissolved in boiling methanol and acetone to destroy excess bromine. The product, 6-bromo-7,8-dimethoxy-3-methyl-2,3,4,5-tetrahydro-1H-3-benzazepine hydrobromide, is allowed to crystallize from the methanol. The hydrobromide is then converted to the corresponding free base.

A mixture of the 6-bromo compound (0.009 mole), trifluoromethyl iodide (0.036 mole) and 0.0708 mole of copper powder in 15 ml. of dimethylformamide in a pressure reactor is heated at 150° C. for 68 hours. The cooled reaction mixture is diluted with 20 ml. of dimethylformamide, 200 ml. of ethyl acetate and then stirred while 500 ml. of water is added. The separated organic phase is washed, dried and evaporated to give 7,8-dimethoxy-3-methyl-6-trifluoromethyl-2,3,4,5-tetrahydro-1H-3-benzazepine which is demethylated in methylene chloride with boron tribromide.

Following the procedures outlined in Example 2 the 7,8-dihydroxy-3-methyl-6-trifluoromethyl-2,3,4,5-tetrahydro-1H-3-benzazepine hydrobromide is treated with 2,3-dichloro-5,6-dicyano-1,4-benzoquinone to give the 7,8-dione which is then reacted with, for example, thiophenol to yield 7,8-dihydroxy-3-methyl-6-phenylthio-9-trifluoromethyl-2,3,4,5-tetrahydro-1H-3-benzazepine hydrobromide.

Similar demethylation of the above prepared 6-bromo compound followed by formation of the quinone and treatment with thiophenol furnishes 9-bromo-7,8-dihydroxy-3-methyl-6-phenylthio-2,3,4,5-tetrahydro-1H-3-benzazepine, free base m.p. 174° C. (dec.).

EXAMPLE 15

To a stirred solution of 42.6 g. (0.206 mole) of 7,8-dimethoxy-2,3,4,5-tetrahydro-1H-3-benzazepine in 1 l. of toluene were added 35.7 ml. of triethylamine (0.256 mole) and 24.5 ml. of ethyl chloroformate (0.256 mole), at room temperature, and the mixture was refluxed for 12 hours. The reaction mixture was filtered to remove triethylamine hydrochloride and the filtrate was concentrated. The solid residue (57 g.) was recrystallized from ethyl acetate to give 3-carboethoxy-7,8-dimethoxy-2,3,4,5-tetrahydro-1H-3-benzazepine, m.p. 91°-93° C.

The above prepared compound (57 g., 0.204 mole) was dissolved in 1 l. of carbon tetrachloride. The solution was cooled to −15° C. and, under a positive argon pressure, 34.2 ml. (0.306 mole) of benzene sulfenyl chloride were added dropwise with stirring. Anhydrous zinc chloride (22.5 g., 0.165 mole) was added all at once and the resulting mixture was stirred at room temperature for 12 hours. An additional 10 ml. of benzene sulfenyl chloride and 11 g. of zinc chloride were added and the mixture was stirred at room temperature for 24 hours. The reaction mixture was filtered, the filtrate was concentrated and the resulting oil was chromotographed on a wet silica column. The product was eluted with increasing concentrations of ethyl acetate in hexane (20–50%) to give 33.3 g. of 3-carboethoxy-7,8-dimethoxy-6-phenylthio-2,3,4,5-tetrahydro-1H-3-benzazepine.

To 700 ml. of tetrahydrofuran containing 12.9 g. (0.34 mole) of lithium aluminum hydride was added dropwise with stirring 32.9 g. (0.085 mole) of the above-prepared 6-phenylthio compound dissolved in 400 ml. of tetrahydrofuran. After the addition was complete the mixture was refluxed for 3 hours and the excess hydride was quenched carefully by the addition of 12.9 ml. of water, 12.9 ml. of 20% sodium hydroxide solution and 38.7 ml. of water. The mixture was filtered and the inorganic solid was washed thoroughly with tetrahydrofuran. The filtrate was concentrated and the resulting oil was chromatographed on silica using methanol/chloroform to give 13 g. of 7,8-dimethoxy-3-methyl-6-phenylthio-2,3,4,5-tetrahydro-1H-3-benzazepine.

To a solution of 13 g. (0.04 mole) of 7,8-dimethoxy-3-methyl-6-phenylthio-2,3,4,5-tetrahydro-1H-3-benzazepine in 750 ml. of methanol was added slowly with stirring at room temperature 316 ml. of a 0.5 M solution of sodium periodate. The reaction mixture was stirred in a water bath heated to 40° C. for 18 hours, filtered and the filtrate was concentrated. The residue was partitioned between chloroform and water, and the aqueous layer was extracted with chloroform. The combined extract was dried over sodium sulfate and evaporated in vacuo to yield 10.4 g. of oil which was triturated with ether to furnish 8.3 g. of solid 7,8-dimethoxy-3-methyl-6-phenylsulfinyl-2,3,4,5-tetrahydro-1H-3-benzazepine, m.p. 128°-132° C.

The above-prepared sulfoxide (8.3 g., 0.024 mole) was dissolved in 200 ml. of methylene chloride. The solution was cooled to −78° C. and, under argon, a solution of 7.9 ml. (0.108 mole) of thionyl chloride in 75 ml. of methylene chloride was added dropwise. The mixture was stirred in the cold for four hours and gradually allowed to warm to room temperature. The reaction mixture was concentrated and the resulting oil was washed with 10% sodium hydroxide solution, then extracted into chloroform. The dried extract was evaporated in vacuo and the residue was chromatographed on silica using methanol/chloroform to give 4.8 g. of 9-chloro-7,8-dimethoxy-3-methyl-6-phenyl-thio-2,3,4,5-tetrahydro-1H-3-benzazepine; hydrochloride salt m.p. 209°-210° C.

To a solution of the above 9-chloro compound (3.76 g., 0.0104 mole) in 120 ml. of methanesulfonic acid was added l-methionine (8.6 g., 0.058 mole). The mixture was stirred at room temperature for 18 hours, quenched with ice/water and made basic with concentrated ammonium hydroxide to pH 9.5. The resulting mixture was extracted with ethyl acetate and the extract was dried over sodium sulfate. Evaporation of the ethyl acetate yielded 1.8 g. (52% crude yield) of 9-chloro-7,8-dihydroxy-3-methyl-6-phenylthio-2,3,4,5-tetrahydro-1H-3-benzazepine, m.p. 174°-176° C., identical to the material prepared in Example 6 above.

EXAMPLE 16

A mixture of 2.6 g. (0.008 mole) of 7,8-dimethoxy-3-methyl-6-phenylthio-2,3,4,5-tetrahydro-1H-3-benzazepine (prepared as in Example 3) and 1.26 g. (0.0085 mole) of dl-methionine in 35 ml. of methanesulfonic acid was stirred at room temperature for 3.5 hours. The reaction mixture was quenched with ice/water, made basic with 10% sodium hydroxide solution to pH 8.5 and extracted with chloroform. The extract was washed with saturated sodium chloride solution, dried over sodium sulfate and evaporated to give 2.18 g. (87% yield) of 8-hydroxy-7-methoxy-3-methyl-6-phenylthio-2,3,4,5-tetrahydro-1H-3-benzazepine, m.p. 161°-162° C.

Reaction of 8-hydroxy-7-methoxy-3-methyl-6-phenylthio-2,3,4,5-tetrahydro-1H-3-benzazepine with acetyl bromide in trifluoroacetic acid gave 8-acetoxy-7-methoxy-3-methyl-6-phenylthio-2,3,4,5-tetrahydro-1H-3-benzazepine; hydrochloride salt m.p. 240°-241° C.

EXAMPLE 17

To a solution of 1.0 g. (0.0078 mole) of p-fluorothiophenol in 200 ml. of methanol was added portionwise 2 g. (0.0073 mole) of 3-methyl-2,3,4,5-tetrahydro-1H-3-benzazepine-7,8-dione hydrobromide (prepared as in Example 2) and the resulting mixture was stirred at room temperature under argon for 1 hour. The methanol was distilled from the reaction mixture in vacuo and the residue was partitioned between ether and water. The aqueous layer was extracted with ether and then made basic with ammonium hydroxide solution. The precipitate was filtered and the dried filtrate was chromatographed on silica using methanol/chloroform. The material eluted from the column was slurried with ether and filtered. Distillation of the ether gave 7,8-dihydroxy-6-(p-fluorophenylthio)-3-methyl-2,3,4,5-tetrahydro-1H-3-benzazepine, m.p. 164°-166° C.

Similarly, reaction of 1 g. (0.0075 mole) of p-toluenethiol and 2 g. of the dione in 200 ml. of methanol as described above gave 7,8-dihydroxy-3-methyl-6-(p-tolylthio)-2,3,4,5-tetrahydro-1H-3-benzazepine, m.p. 105°–114° C. and reaction of 1.65 g. (0.0011 mole) of p-nitrothiophenol and 2.3 g. of the dione in 200 ml. of methanol gave 7,8-dihydroxy-3-methyl-6-(p-nitrophenylthio)-2,3,4,5-tetrahydro-1H-3-benzazepine, m.p. 165°–170° C.

Reaction of 7,8-dihydroxy-6-(p-fluorophenylthio)-3-methyl-2,3,4,5-tetrahydro-1H-3-benzazepine with acetyl bromide as described in Example 4 yielded 7,8-diacetoxy-6-(p-fluorophenylthio)-3-methyl-2,3,4,5-tetrahydro-1H-3-benzazepine, m.p. 125°–127° C.

EXAMPLE 18

Following the procedures outlined in Example 17, 0.9 g. (0.0075 mole) of furfuryl mercaptan and 2 g. (0.0073 mole) of 3-methyl-2,3,4,5-tetrahydro-1H-3-benzazepine-7,8-dione hydrobromide were reacted in 200 ml. of methanol to yield 7,8-dihydroxy-6-furfurylthio-3-methyl-2,3,4,5-tetrahydro-1H-3-benzazepine, free base m.p. 162°–165° C.

EXAMPLE 19

To a solution of 1.3 g. (0.02 mole) of potassium hydroxide in 20 ml. of water was added 2.9 g. (0.022 mole) of p-fluorothiophenol in 20 ml. of ethanol. The mixture was refluxed for 1 hour and 4.8 g. (0.02 mole) of 6-chloro-3-methyl-9-nitro-2,3,4,5-tetrahydro-1H-3-benzazepine (prepared as in Example 9) in 20 ml. of ethanol was added. The resulting solution was refluxed for 4.5 hours and allowed to cool. A red oil was decanted from the reaction mixture, dissolved in ethyl acetate and washed with saturated sodium chloride solution and 10% sodium hydroxide solution. The dried ethyl acetate solution was evaporated to give 5.3 g. of 6-(p-fluorophenylthio)-3-methyl-9-nitro-2,3,4,5-tetrahydro-1H-3-benzazepine. A mixture of 4.3 g. (0.0135 mole) of the above prepared 9-nitro derivative dissolved in 100 ml. of ethanol, 50 ml. of 1 N sulfuric acid and 0.4 g. of 5% palladium-on-carbon in 50 ml. of ethanol was hydrogenated at 60 p.s.i. for 2 hours. The catalyst was filtered from the reaction mixture and the filtrate was evaporated. The residue was dissolved in a minimum amount of ethanol to which ethereal hydrogen chloride was added. The solid was filtered to give 1.5 g. of 9-amino-6-(p-fluorophenylthio)-3-methyl-2,3,4,5-tetrahydro-1H-3-benzazepine dihydrochloride.

Following the procedure outlined in Example 9, the 9-amino-3-benzazepine dihydrochloride (1.25 g.) was diazotized with sodium nitrate in water and concentrated hydrochloric acid and then treated with cuprous chloride to yield, after purification on silica, 9-chloro-6-(p-fluorophenylthio)-3-methyl-2,3,4,5-tetrahydro-1H-3-benzazepine; hydrochloride salt m.p. 212°–213° C.

EXAMPLE 20

To a solution of 34 g. (0.177 mole) of 7,8-dimethoxy-3-methyl-2,3,4,5-tetrahydro-1H-3-benzazepine in 200 ml. of trifluoroacetic acid was added 40 ml. of bromine (118 g., 0.735 mole) in 200 ml. of acetic acid and the solution was refluxed for 2 hours on a steam bath. The reaction mixture was quenched with 40% sodium hydroxide solution to pH 8 and then extracted with ethyl acetate. The extract was washed with water, dried and evaporated to leave 6,9-dibromo-7,8-dimethoxy-3-methyl-2,3,4,5-tetrahydro-1H-3-benzazepine; hydrochloride salt m.p. 219°–220° C.

A sample of 9.7 g. (0.0256 mole) of the above 6,9-dibromo compound was evaporated three times from dry methylene chloride. After being dried with magnesium sulfate, the methylene chloride solution was evaporated and the residue was dissolved in 200 ml. of dry toluene. The solution was stirred under argon at −78° C. and 9.82 ml. (0.0256 mole) of fresh n-butyl lithium solution in hexane was added. To the resulting cold solution was added 20 g. (0.0917 mole) of diphenyl disulfide and the mixture was stirred for 1 hour. The reaction mixture was quenched with 10% hydrochloric acid and extracted with ether. The aqueous solution was made basic and extracted with ethyl acetate. The extract was washed with water, dried and evaporated to give 6.3 g. of crude oil which was chromatographed on silica with ethyl acetate. The resulting oil was passed quickly through a column containing alumina with ethyl acetate and the solution was evaporated. The residue was taken into ether and treated with ethereal hydrogen chloride to give 9-bromo-7,8-dimethoxy-3-methyl-6-phenylthio-2,3,4,5-tetrahydro-1H-3-benzazepine hydrochloride, m.p. 201°–203° C.

A mixture of 1.03 g. (0.0023 mole) of the above prepared hydrochloride, 100 ml. of methanesulfonic acid, 5 ml. of water and 4 g. (0.027 mole) of methionine was stirred at room temperature for 72 hours. The reaction mixture was poured onto ice, made basic with ammonium hydroxide solution to pH 7 and extracted with ethyl acetate. The extract was washed with aqueous sodium bisulfite and water, dried and evaporated to yield 600 mg. of 9-bromo-7,8-dihydroxy-3-methyl-6-phenylthio-2,3,4,5-tetrahydro-1H-3-benzazepine, m.p. 174° C. (dec.).

EXAMPLE 21

To a solution of 1.1 g. (0.0011 mole) of 2-furanthiol in 200 ml. of methanol is added portionwise 2.3 g. (0.0084 mole) of 3-methyl-2,3,4,5-tetrahydro-1H-3-benzazepine-7,8-dione hydrobromide. After stirring for 1 hour at room temperature the reaction mixture is filtered and the filtrate concentrated in vacuo to give 7,8-dihydroxy-6-(2-furylthio)-3-methyl-2,3,4,5-tetrahydro-1H-3-benzazepine hydrobromide.

Similarly reaction of 1.44 g. (0.0011 mole) of 2-thiophenemethanethiol in 200 ml. of methanol and the above dione (2.3 g., 0.0084 mole) gives 7,8-dihydroxy-3-methyl-6-(2-thienylmethylthio)-2,3,4,5-tetrahydro-1H-3-benzazepine hydrobromide.

EXAMPLE 22

To a solution of 12.8 g. (0.052 mole) of 7,8-dimethoxy-2,3,4,5-tetrahydro-1H-3-benzazepine (prepared as in Example 1) in 50 ml. of glacial acetic acid at 55° C. was added 3.0 ml. of bromine (8.8 g., 0.055 mole) dropwise over 1 hour with stirring. After addition was completed, the temperature was raised to 70° C. for 2 hours. The reaction mixture was poured into ice/water and made basic with 40% sodium hydroxide solution. The basic solution was extracted with ethyl acetate and the extract dried over sodium sulfate. Removal of the solvent gave 6-bromo-7,8-dimethoxy-2,3,4,5-tetrahydro-1H-3-benzazepine as an oil.

A solution of 1.0 g. (0.0035 mole) of the 6-bromo compound prepared above in 20 ml. of dry tetrahydrofuran was added to 2.0 ml. of a 2.3 M solution of n-butyl lithium in hexane at −78° C. under argon over a 1 hour period. The mixture was stirred for an additional 30 minutes and then 2.9 g. (0.0079 mole) of diphenyl disulfide in 10 ml. of tetrahydrofuran was added dropwise. This mixture was stirred at −78° C. for 2 hours, allowed to stand at room temperature for 18 hours and then slowly poured into a mixture of ice/water (50 ml.) and ether (25 ml.). The aqueous layer was extracted with ether, and the ether extract was extracted with 3 N hydrochloric acid. The acid layer was made basic with sodium hydroxide solution and extracted with ethyl acetate. The dried extract was concentrated to dryness to leave 7,8-dimethoxy-6-phenylthio-2,3,4,5-tetrahydro-1H-3-benzazepine.

Ethylene oxide (0.5 ml., 0.44 g., 0.010 mole) is added to a stirred solution of 1.58 g. (0.005 mole) of 7,8-dimethoxy-6-phenylthio-2,3,4,5-tetrahydro-1H-3-benzazepine in 100 ml. of methanol at 0° C. The mixture is stirred at this temperature for 2 hours and then allowed to warm to room temperature. Concentration of the mixture in vacuo gives 7,8-dimethoxy-3-(2-hydroxyethyl)-6-phenylthio-2,3,4,5-tetrahydro-1H-3-benzazepine.

The above prepared benzazepine (1.66 g., 0.005 mole) is refluxed in 25 ml. of 48% hydrobromic acid for 2 hours. The reaction mixture is evaporated to dryness in vacuo and the residue distilled azeotropically with toluene to leave the product, 7,8-dihydroxy-3-(2-hydroxyethyl)-6-phenylthio-2,3,4,5-tetrahydro-1H-3-benzazepine hydrobromide.

EXAMPLE 23

To a solution of 1.58 g. (0.005 mole) of 7,8-dimethoxy-6-phenylthio-2,3,4,5-tetrahydro-1H-3-benzazepine in 25 ml. of methylene chloride and 1.0 g. of triethylamine is added dropwise 1.05 g. (0.010 mole) of cyclopropanecarboxylic acid chloride at 5° C. and the mixture is stirred at room temperature for 3 hours. The reaction mixture is filtered and the filtrate is washed with water, 5% potassium carbonate solution and then with water, dried and subsequently concentrated to give 3-cyclopropanecarbonyl-7,8-dimethoxy-6-phenylthio-2,3,4,5-tetrahydro-1H-3-benzazepine.

The cyclopropanecarbonyl derivative (1.85 g., 0.005 mole) in 10 ml. of dry tetrahydrofuran is added to 20 ml. of a 1.02 M solution of diborane in tetrahydrofuran (0.02 mole) at 0° C. and under argon. The mixture is allowed to come to room temperature and then refluxed for 3 hours. The cooled reaction mixture is treated with methanol and 3 N hydrochloric acid to decompose excess diborane and refluxed for 1 hour. This mixture is evaporated to dryness and the residue is taken up into water, then extracted with ether. The aqueous layer is made basic with sodium hydroxide solution, extracted with methylene chloride, dried and concentrated to leave 3-cyclopropylmethyl-7,8-dimethoxy-6-phenylthio-2,3,4,5-tetrahydro-1H-3-benzazepine. Demethylation with 48% hydrobromic acid as described in Example 24 yields 3-cyclopropylmethyl-7,8-dihydroxy-6-phenylthio-2,3,4,5-tetrahydro-1H-3-benzazepine hydrobromide.

EXAMPLE 24

To a solution of 1.58 g. (0.005 mole) of 7,8-dimethoxy-6-phenylthio-2,3,4,5-tetrahydro-1H-3-benzazepine in 25 ml. of methylene chloride and 1.0 g. of triethylamine is added dropwise 1.85 g. (0.010 mole) of 2-phenethylbromide at 5° C. The mixture is stirred at room temperature for 3 hours, filtered and the filtrate is washed with water, then extracted with dilute hydrochloric acid. The acid extract is washed with ether and made basic with 10% sodium hydroxide solution to give the product 7,8-dimethoxy-3-(2-phenethyl)-6-phenylthio-2,3,4,5-tetrahydro-1H-3-benzazepine. Demethylation with 48% hydrobromic acid as described in Example 24 yields 7,8-dihydroxy-3-(2-phenethyl)-6-phenylthio-2,3,4,5-tetrahydro-1H-3-benzazepine hydrobromide.

EXAMPLE 25

A solution of 5.0 g. (0.0396 mole) of m-fluoroanisole in 44 ml. of dry tetrahydrofuran was treated with 14.5 ml. of 2.6 M solution of n-butyl lithium in hexane at −65° C., and the resulting mixture was stirred in the cold for 2¼ hours. Trimethylborate ester (6.41 g., 0.0377 mole) in 52 ml. of dry ther was added at −65° C. over a 15 minute period. The reaction mixture was allowed to warm to room temperature, and dilute hydrochloric acid was added. The organic layer was separated, washed with water, dried and concentrated to give 3-fluoro-2-(dihydroxyborinyl)anisole (4.62 g., 80% yield).

To a solution of the above prepared anisole (4.55 g., 0.0268 mole) in 33 ml. of warm toluene was added slowly 12.4 ml. of 30% hydrogen peroxide solution, and the mixture was heated on a steam bath for 45 minutes. The reaction mixture was cooled, and the separated organic layer was washed with water, 10% ferrous ammonium sulfate solution and water. The organic solution was then extracted with 10% sodium hydroxide solution, and the basic extract was made acid with concentrated hydrochloric acid to give an oil. The oil was extracted with methylene chloride, dried and concentrated to leave 3-fluoro-2-hydroxyanisole (2.04 g., 69% yield).

The hydroxyanisole derivative (1.77 g., 0.0125 mole) was dissolved in 18 ml. of dry acetone, and 3.44 g. of powdered potassium carbonate and 2.36 ml. of methyl sulfate were added. The mixture was stirred and refluxed for 30 minutes, diluted with water and extracted with ether. The ether extract was washed with water, stirred for 90 minutes with dilute ammonium hydroxide solution, and the separated organic layer was washed with water. The dried organic solution was concentrated to 1.64 g. (68% yield) of liquid, 3-fluoro-2-methoxyanisole, b.p. 93.5°–102° C. at 19–24 mm. of mercury pressure.

A solution of 37% formaldehyde (25 ml.) was added to a solution of the above prepared methoxyanisole (25.0 g., 0.16 mole) in 100 ml. of glacial acetic acid and hydrogen chloride gas was bubbled in for 4½ hours. The temperature was maintained at 20°–25° C. by means of an ice/water bath. The reaction mixture was poured into water, extracted with ether and the ether extract washed with water. The dried extract was concentrated at 35° C. to leave 31.63 g. (97% yield) of 3,4-dimethoxy-2-fluorobenzyl chloride, m.p. 44.5°–47.5° C.

Sodium cyanide (9.19 g., 0.187 mole) was added to a solution of the above benzyl chloride (30.7 g., 0.15 mole) in 530 ml. of dimethyl sulfoxide. After about 45 minutes, the reaction mixture was poured into 1 l. ice/water and extracted with ether. The ether extract was washed with water, dried and concentrated at 50° C. to give 26.9 g. (92% yield) of 3,4-dimethoxy-2-fluorobenzyl nitrile.

The benzyl nitrile (3.9 g., 0.02 mole) was dissolved in equal volumes of ethanol and 10 N aqueous sodium hydroxide (50 ml. of each) and refluxed for 24 hours. The reaction mixture was poured into about 200 ml. of hot water, filtered, and the hot filtrate was acidified with concentrated hydrochloric acid. Cooling yielded 2-fluorohomoveratric acid.

Following the procedures outlined in Examples 1 and 2, the 2-fluorohomoveratric acid is reacted with aminoacetaldehyde dimethylacetal to form N-(2,2-dimethoxyethyl)-3,4,-dimethoxy-2-fluorophenylacetamide which is ring closed with hydrochloric acid and glacial acetic acid to obtain 2,3-dihydro-7,8-dimethoxy-6-fluoro-2-oxo-1H-3-benzazepine. The dihydrobenzazepine is reduced first with hydrogen and palladium-on-carbon, then with diborane to give 7,8-dimethoxy-6-fluoro-2,3,4,5-tetrahydro-1H-3-benzazepine. The latter is treated with formaldehyde/formic acid to give the corresponding 3-methyl derivative which is demethylated with 48% hydrobromic acid. The resulting catechol is oxidized with 2,3-dichloro-5,6-dicyano-1,4-benzoquinone and the dione is treated with a methanolic solution of thiophenol to furnish the product 7,8-dihydroxy-9-fluoro-3-methyl-6-phenyl-thio-2,3,4,5-tetrahydro-1H-3-benzazepine.

EXAMPLE 26

Following the procedures outlined in Example 2, a methanolic solution of p-methoxythiophenol is reacted with 3-methyl-2,3,4,5-tetrahydro-1H-3-benzazepine-7,8-dione hydrobromide to yield the product, as the free base, 7,8-dihydroxy-6-(p-methoxyphenylthio)-3-methyl-2,3,4,5-tetrahydro-1H-3-benzazepine. Treatment with boron tribromide in methylene chloride solution gives 7,8-dihydroxy-6-(p-hydroxyphenylthio)-3-methyl-2,3,4,5-tetrahydro-1H-3-benzazepine.

EXAMPLE 27

To a solution of 18.21 g. (0.0446 mole) of 9-bromo-7,8-dimethoxy-3-methyl-6-phenylthio-2,3,4,5-tetrahydro-1H-3-benzazepine (prepared as in Example 20) in 200 ml. of toluene, cooled to −78° C., is slowly added 26.0 ml. of 2.1 M n-butyl lithium in hexane. After 20 minutes at this temperature 23.1 ml. of dimethylformamide is added and the mixture is stirred for ½ hour. The reaction mixture, at room temperature, is poured into 10% sodium hydroxide solution and extracted with ethyl acetate. The extract is washed with water, dried and concentrated to give 7,8-dimethoxy-3-methyl-6-phenylthio-2,3,4,5-tetrahydro-1H-3-benzazepine-9-carboxaldehyde.

The aldehyde (10.72 g., 0.03 mole) is dissolved in 50 ml. of methanol and 3.42 g. (0.09 mole) of sodium borohydride is added slowly. The mixture is stirred for 1 hour, quenched with acetic acid, evaporated, made basic and extracted with ethyl acetate. The extract is washed with water, dried and evaporated to leave 7,8-dimethoxy-9-hydroxymethyl-3-methyl-6-phenylthio-2,3,4,5-tetrahydro-1H-3-benzazepine.

A mixture of 5.39 g. (0.015 mole) of the above 9-hydroxymethyl derivative in 100 ml. of chloroform and 75 ml. of concentrated hydrochloric acid is refluxed for 2 hours. The reaction mixture is evaporated and partitioned between hydrochloric acid and ethyl acetate. The acid solution is made basic with 40% sodium hydroxide solution and extracted with ethyl acetate. The extract is washed with water, dried and evaporated to give 9-chloromethyl-7,8-dimethoxy-3-methyl-6-phenylthio-2,3,4,5-tetrahydro-1H-3-benzazepine.

To a solution of 3.77 g. (0.01 mole) of the 9-chloromethyl derivative is added slowly 1.4 g (0.036 mole) of sodium borohydride and the mixture is heated on a steam bath under argon for 3 hours. The reaction mixture is extracted with aqueous ethyl acetate, and the extract is washed with water. The dried extract is then evaporated to yield 7,8-dimethoxy-3,9-dimethyl-6-phenylthio-2,3,4,5-tetrahydro-1H-3-benzazepine.

A solution of 1.717 g. (0.,005 mole) of the 9-methyl benzazepine in ethyl acetate is treated with ethereal hydrogen chloride and then evaporated. The residue is dissolved in 25 ml. of dry methylene chloride, cooled to 0° C. and 9.23 ml. of a solution of 1 g. of boron tribromide per 2.5 ml. of methylene chloride (0.015 mole) is added. After 10 minutes the reaction mixture is evaporated and the residue extracted with ethyl acetate/water/ammonium hydroxide. The ethyl acetate extract is washed with water, dried and evaporated to give 7,8-dihydroxy-3,9-dimethyl-6-phenylthio-2,3,4,5-tetrahydro-1H-3-benzazepine.

EXAMPLE 28

To a solution of 0.8 g. (0.0022 mole) of 9-chloro-7,8-dimethoxy-3-methyl-6-phenylthio-2,3,4,5-tetrahydro-1H-3-benzazepine (prepared as in Example 15) in 10 ml. of methylsulfonic acid at room temperature is added 0.35 g. (0.0023 mole) of solid methionine all at once and the mixture is stirred for 4 hours. The reaction mixture is quenched in ice/water and made basic (pH 7.5) with concentrated ammonium hydroxide. The basic solution is extracted with methylene chloride and washed with saturated sodium chloride solution. The organic layer is dried and evaporated in vacuo to leave 9-chloro-8-hydroxy-7-methoxy-3-methyl-6-phenylthio-2,3,4,5-tetrahydro-1H-3-benzazepine.

EXAMPLE 29

A mixture of 0.45 g. (0.0013 mole) of 9-chloro-8-hydroxy-7-methoxy-3-methyl-6-phenylthio-2,3,4,5-tetrahydro-1H-3-benzazepine and 0.2 ml. (0.0026 mole) of acetyl bromide in trifluoroacetic acid is heated to reflux on a steam bath for 2 hours. The reaction mixture is concentrated and the residue is taken up in 100 ml. of methylene chloride. This solution is dried and evaporated to give 8-acetoxy-9-chloro-7-methoxy-3-methyl-6-phenylthio-2,3,4,5-tetrahydro-1H-3-benzazepine.

EXAMPLE 30

| Ingredients | Mg. per Capsule |
| --- | --- |
| 7,8-dihydroxy-6-phenylthio 2,3,4,5-tetrahydro-1H-3-benzazepine (as an acid addition salt) | 50 (free base) |
| Magnesium stearate | 2 |
| Lactose | 200 |

The above ingredients are mixed, passed through a #40 mesh screen, remixed and filled into #2 capsules.

EXAMPLE 31

| Ingredients | Mg. per Tablet |
| --- | --- |
| 7,8-dihydroxy-3-methyl-6-phenylthio-2,3,4,5-tetrahydro-1H-3-benzazepine (as an acid addition salt) | 10 |

| Ingredients | Mg. per Tablet |
| --- | --- |
| Calcium sulfate, dihydrate | 150 |
| Sucrose | 25 |
| Starch | 15 |
| Talc | 5 |
| Stearic acid | 3 |

The sucrose, calcium sulfate and active ingredient are thoroughly mixed and granulated with hot 10% gelatin solution. The wetted mass is passed through a #6 mesh screen directly onto drying trays. The granules are dried at 50° C. and passed through a #20 mesh screen, mixed with the starch, talc and stearic acid, and compressed into tablets.

The capsules or tablets prepared as in Examples 30 and 31 are administered internally to an animal or human subject requiring antipsychotic or antiemetic therapy within the dose ranges as set forth hereinabove. Similarly other compounds of formula I can be formulated in the same manner to give pharmaceutical compositions useful in producing dopamine receptor blocking activity.

We claim:

1. A compound represented by the formula:

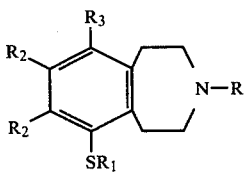

wherein:
R is methyl, allyl, dimethylallyl, phenethyl, cyclopropylmethyl or β-hydroxyethyl;
$R_1$ is phenyl, m- or p-substituted phenyl with the substituent being trifluoromethyl, chloro, methoxy, methyl, fluoro, nitro or hydroxy or cyclohexyl;
$R_2$ is hydrogen, methoxy, alkanoyloxy with the alkanoyl moiety having from 2 to 6 carbon atoms, or hydroxy, each $R_2$ being the same or different except that when one of $R_2$ is alkanoyloxy the other is hydrogen, methoxy or alkanoyloxy; and
$R_3$ is hydrogen, chloro, bromo, trifluoromethyl, fluoro or methyl,
or a nontoxic pharmaceutically acceptable acid addition salt thereof.

2. A compound according to claim 1 in which R is methyl, $R_1$ is phenyl, p-trifluoromethylphenyl, p-chlorophenyl, p-tolyl, p-fluorophenyl or cyclohexyl both $R_2$ are hydrogen, acetoxy or hydroxy, or one $R_2$ is hydroxy and the other is methoxy, and $R_3$ is hydrogen, chloro or bromo.

3. A compound according to claim 2 in which both $R_2$ are hydroxy, or one $R_2$ is hydroxy and the other is methoxy.

4. A compound according to claim 3 in which both $R_2$ are hydroxy.

5. A compound according to claim 3 being the compound 8-hydroxy-7-methoxy-3-methyl-6-phenylthio-2,3,4,5-tetrahydro-1H-3-benzazepine.

6. A compound according to claim 4 being the compound 7,8-dihydroxy-3-methyl-6-phenylthio-2,3,4,5-tetrahydro-1H-3-benzazepine.

7. A compound according to claim 4 being the compound 9-chloro-7,8-dihydroxy-3-methyl-6-phenylthio-2,3,4,5-tetrahydro-1H-3-benzazepine.

8. A compound according to claim 4 being the compound 6-(p-fluorophenylthio)-7,8-dihydroxy-3-methyl-2,3,4,5-tetrahydro-1H-3-benzazepine.

9. A compound according to claim 4 being the compound 9-bromo-7,8-dihydroxy-3-methyl-6-phenylthio-2,3,4,5-tetrahydro-1H-3-benzazepine.

10. A compound according to claim 2 in which both $R_2$ are hydrogen.

11. A compound according to claim 10 being the compound 3-methyl-6-phenylthio-2,3,4,5-tetrahydro-1H-3-benzazepine.

12. A pharmaceutical composition having dopamine receptor blocking activity in dosage unit form comprising a pharmaceutical carrier and a nontoxic amount sufficient to produce said activity of a compound of claims 1, 6, 7, 8, 9, 11 or 5, or a pharmaceutically acceptable acid addition salt of said compound.

13. A method of producing dopamine receptor blocking activity which comprises administering internally to an animal or human subject in need of such activity a compound of claims 1, 6, 7, 8, 9, 11 or 5, or a pharmaceutically acceptable acid addition salt of said compound, in a nontoxic amount sufficient to produce said activity.

* * * * *